(12) United States Patent
Adams et al.

(10) Patent No.: US 10,410,745 B2
(45) Date of Patent: Sep. 10, 2019

(54) MEDICAL DEVICE ASSOCIATION SYSTEMS AND METHODS

(71) Applicant: Smiths Medical ASD, Inc., Plymouth, MN (US)

(72) Inventors: Grant Adams, Plymouth, MN (US); Larry Zalesky, Plymouth, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 98 days.

(21) Appl. No.: 15/508,831

(22) PCT Filed: Aug. 26, 2015

(86) PCT No.: PCT/US2015/046918
§ 371 (c)(1),
(2) Date: Mar. 3, 2017

(87) PCT Pub. No.: WO2016/036554
PCT Pub. Date: Mar. 10, 2016

(65) Prior Publication Data
US 2017/0277851 A1    Sep. 28, 2017

Related U.S. Application Data

(60) Provisional application No. 62/045,379, filed on Sep. 3, 2014.

(51) Int. Cl.
*G06F 3/01*      (2006.01)
*A61M 5/14*     (2006.01)
(Continued)

(52) U.S. Cl.
CPC .......... *G16H 40/40* (2018.01); *A61M 5/1407* (2013.01); *G01P 15/18* (2013.01); *G06F 3/017* (2013.01);
(Continued)

(58) Field of Classification Search
CPC ...... G01P 15/18; G06H 40/40; A61M 5/1407; A61M 5/14276; A61M 5/142;
(Continued)

(56) References Cited

U.S. PATENT DOCUMENTS

| 8,793,623 B2 | 7/2014 | Halbert et al. |
| 2004/0133079 A1* | 7/2004 | Mazar .................. A61B 5/0031 600/300 |

(Continued)

FOREIGN PATENT DOCUMENTS

EP    2 674 178 A1    12/2013

OTHER PUBLICATIONS

Search Report dated Mar. 13, 2018 for EP Application No. 15838922.1, 8 pages.
(Continued)

*Primary Examiner* — Helen C Kwok
(74) *Attorney, Agent, or Firm* — Patterson Thuente Pedersen, P.A.

(57) ABSTRACT

A method for associating medical devices is provided. The method can include providing a plurality of medical devices and each of the medical devices can include an accelerometer configured to measure spatial accelerations of the medical device. Each of at least two of the medical devices can measure with its accelerometer an acceleration pattern with respect to time. The method can include comparing for correspondence, according to defined correspondence criteria, the measured acceleration patterns, and associating all of the medical devices that measured acceleration patterns that satisfy the defined correspondence criteria. The method can also include modifying a parameter of each member of a set of devices that are associated.

15 Claims, 3 Drawing Sheets

(51) Int. Cl.
    *G06F 19/00* (2018.01)
    *G16H 40/40* (2018.01)
    *G01P 15/18* (2013.01)

(52) U.S. Cl.
    CPC .......... *G06F 19/00* (2013.01); *G06F 19/3468* (2013.01); *A61M 2205/332* (2013.01); *A61M 2205/3317* (2013.01); *A61M 2205/502* (2013.01); *G06F 3/01* (2013.01)

(58) Field of Classification Search
    CPC ........ A61M 5/168; G06F 3/017; G06F 19/00; A61B 5/0006; A61B 5/0031; A61B 5/02055; A61B 5/4546; A61B 5/0205; A61B 5/0402; A61B 5/0809; A61B 5/1116
    See application file for complete search history.

(56) References Cited

U.S. PATENT DOCUMENTS

| | | | |
|---|---|---|---|
| 2006/0227030 A1 | 10/2006 | Clifford et al. | |
| 2007/0287386 A1* | 12/2007 | Agrawal | H04W 76/14 455/67.11 |
| 2008/0004904 A1* | 1/2008 | Tran | A61B 5/0006 705/2 |
| 2008/0046018 A1* | 2/2008 | Von Huben | A61M 1/122 607/27 |
| 2009/0157622 A1 | 6/2009 | Roberts et al. | |
| 2010/0280417 A1* | 11/2010 | Skelton | A61M 5/14276 600/595 |
| 2011/0054290 A1* | 3/2011 | Derchak | A61B 5/0002 600/388 |
| 2011/0066007 A1* | 3/2011 | Banet | A61B 5/0402 600/301 |
| 2013/0046871 A1 | 2/2013 | Vik et al. | |
| 2013/0211205 A1 | 8/2013 | Havel et al. | |
| 2014/0066816 A1* | 3/2014 | McNames | A61B 5/002 600/595 |
| 2014/0104156 A1 | 4/2014 | Touma et al. | |
| 2014/0164519 A1* | 6/2014 | Shah | H04L 67/306 709/204 |
| 2015/0360041 A1* | 12/2015 | Stahmann | A61N 1/3962 607/4 |
| 2016/0250490 A1* | 9/2016 | Hoffman | A61N 1/37252 607/60 |
| 2016/0291704 A1* | 10/2016 | Jackson | G06F 3/0383 |
| 2017/0150939 A1* | 6/2017 | Shah | A61B 6/548 |
| 2018/0015218 A1 | 1/2018 | Welsch | |

OTHER PUBLICATIONS

International Search Report for corresponding International Application No. PCT/US2015/046918 dated Dec. 4, 2015; 3 pages.
Written Opinion of the International Searching Authority for corresponding International Application No. PCT/US2015/046918 dated Dec. 4, 2015; 5 pages.

* cited by examiner

Fig. 2

*Fig. 3*

MEDICAL DEVICE ASSOCIATION SYSTEMS AND METHODS

CROSS REFERENCE TO RELATED APPLICATIONS

The present application is a National Phase entry of PCT/US2015/046918, filed on Aug. 26, 2015, which claims the benefit of U.S. Provisional Application No. 62/045,379 filed on Sep. 3, 2014, which are hereby incorporated herein in their entirety by reference.

TECHNICAL FIELD

This disclosure relates to medical devices, and more particularly, to systems and methods for associating medical devices.

BACKGROUND

In medical caregiving, multiple microprocessor-controlled medical devices may be used at the same time to provide care for a single patient. In some patient populations it may be common to have, for example, six to nine infusion pumps in use at one time to provide therapy to a single patient; and in some cases, even ten to twenty infusion pumps could be in use with a single patient. Other medical devices, such as breathing equipment and monitoring units, may be in use with the patient as well. In some cases, it may be desirable to associate the medical devices so that they may operate and/or be controlled in a coordinated manner, which may simplify workflows for caregivers.

Present techniques for associating at least one medical device with at least one other medical device may include multiple steps, such as interacting individually with each device to be associated. In view of the goal of simplifying caregiver workloads, it would be desirable to provide improved systems and methods for associating medical devices which would, for example, minimize required interactions with the devices to achieve their associations.

SUMMARY

This disclosure relates to medical devices, and more particularly, to systems and methods for associating medical devices.

In an illustrative but non-limiting example, the disclosure provides a method for associating medical devices. The method can include providing a plurality of medical devices and each of the medical devices can include an accelerometer configured to measure spatial accelerations of the medical device. The method can include each of at least two of the medical devices measuring with its accelerometer an acceleration pattern with respect to time. The method can include comparing for correspondence, according to defined correspondence criteria, the measured acceleration patterns. The method can include associating all of the medical devices that measured acceleration patterns that satisfy the defined correspondence criteria. The method can also include modifying a parameter of each member of a set of devices that are associated.

In the method of associating medical devices, comparing can include scaling at least one of the measured acceleration patterns, and/or performing a coordinate transformation on at least one of the measured acceleration patterns.

In the method of associating medical devices, at least one of plurality of medical devices can include an accelerometer that measures acceleration in more than one axis.

In the method of associating medical devices, at least one of plurality of medical devices can include an accelerometer that measures acceleration in fewer than three axes.

In the method of associating medical devices, the plurality of medical devices can include medical devices in an association-accepting mode.

In the method of associating medical devices, comparing can include each of the at least two of the plurality of medical devices transmitting the acceleration pattern that it measured to an information system, and the information system comparing for correspondence, according to defined correspondence criteria, the acceleration patterns transmitted from each of the at least two of the plurality of medical devices. The method can also include the information system communicating an associating message to at least each of the at least two of the plurality of medical devices that measured acceleration patterns that satisfy the defined correspondence criteria.

In the method of associating medical devices, comparing can be performed in a distributed manner among the at least two of the plurality of medical devices.

In the method of associating medical devices, comparing can be performed by one of the at least two of the plurality of medical devices.

In the method of associating medical devices, comparing can include at least a first one of the at least two of the plurality of medical devices transmitting information related to the acceleration pattern measured with its accelerometer. Comparing can include at least a second one of the at least two of the plurality of medical devices comparing information related to the acceleration pattern measured with its accelerometer with information received from the first one of the at least two of the plurality of medical devices.

The method of associating medical devices can also include mechanically mounting the devices of the plurality of medical devices to a common support structure.

In another illustrative but non-limiting example, the disclosure provides a system of medical devices including a plurality of medical devices and an information system. Each of the plurality of medical devices can include an accelerometer configured to measure spatial accelerations of the medical device, a controller operatively coupled to the accelerometer, and a communication interface operatively coupled to the controller. The information system can be communicatively coupled to the communication interface of each of the plurality of medical devices. The controller of each of the plurality of medical devices is configured and programmed to process an acceleration pattern measured by the accelerometer of the medical device, and communicate information related to the acceleration pattern to the information system via the communication interface. The information system can be configured and programmed to receive the information related to the acceleration patterns communicated by members of the plurality of medical devices, compare for correspondence, according to defined correspondence criteria, the information related to the acceleration patterns received by the information system, and maintain a list of at least each of the plurality of medical devices that communicated information related to the acceleration pattern that satisfies the defined correspondence criteria. In some cases, at least one of the plurality of medical devices can include a selectively actuatable component capable of producing measurable accelerations in others of the plurality of medical devices when the plurality of medical devices are mounted to a common support structure.

In some instances, the information system is configured and programmed to communicate an associating message to at least each medical device that communicated information related to the acceleration pattern that satisfies the defined correspondence criteria, and the controller of each of the plurality of medical devices is configured and programmed to receive the associating message from the information system.

In yet another illustrative but non-limiting example, the disclosure provides a method for associating medical devices. The method can include mounting a plurality of medical devices to a common support structure. Each of the plurality of medical devices can include an accelerometer configured to measure spatial accelerations of the medical device. The method can include imparting a mechanical impulse to the plurality of medical devices. The mechanical impulse can be transmitted between all of the plurality of medical devices through the common support structure. The method can include each of the plurality of medical devices measuring with its accelerometer an acceleration pattern associated with the mechanical impulse. The method can include comparing the acceleration patterns measured by each of the plurality of medical devices for correspondence, according to defined correspondence criteria. The method can include associating all of the plurality of medical devices that measured acceleration patterns that satisfy the defined correspondence criteria. In some cases, imparting the mechanical impulse can include manually striking the common support structure. In some cases, imparting the mechanical impulse can include a component of one of the plurality of medical devices producing the mechanical impulse.

The above summary is not intended to describe each and every example or every implementation of the disclosure. The Description that follows more particularly exemplifies various illustrative embodiments.

BRIEF DESCRIPTION OF THE FIGURES

The following description should be read with reference to the drawings. The drawings, which are not necessarily to scale, depict several examples and are not intended to limit the scope of the disclosure. The disclosure may be more completely understood in consideration of the following description with respect to various examples in connection with the accompanying drawings, in which.

DESCRIPTION

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized.

Figure 1:
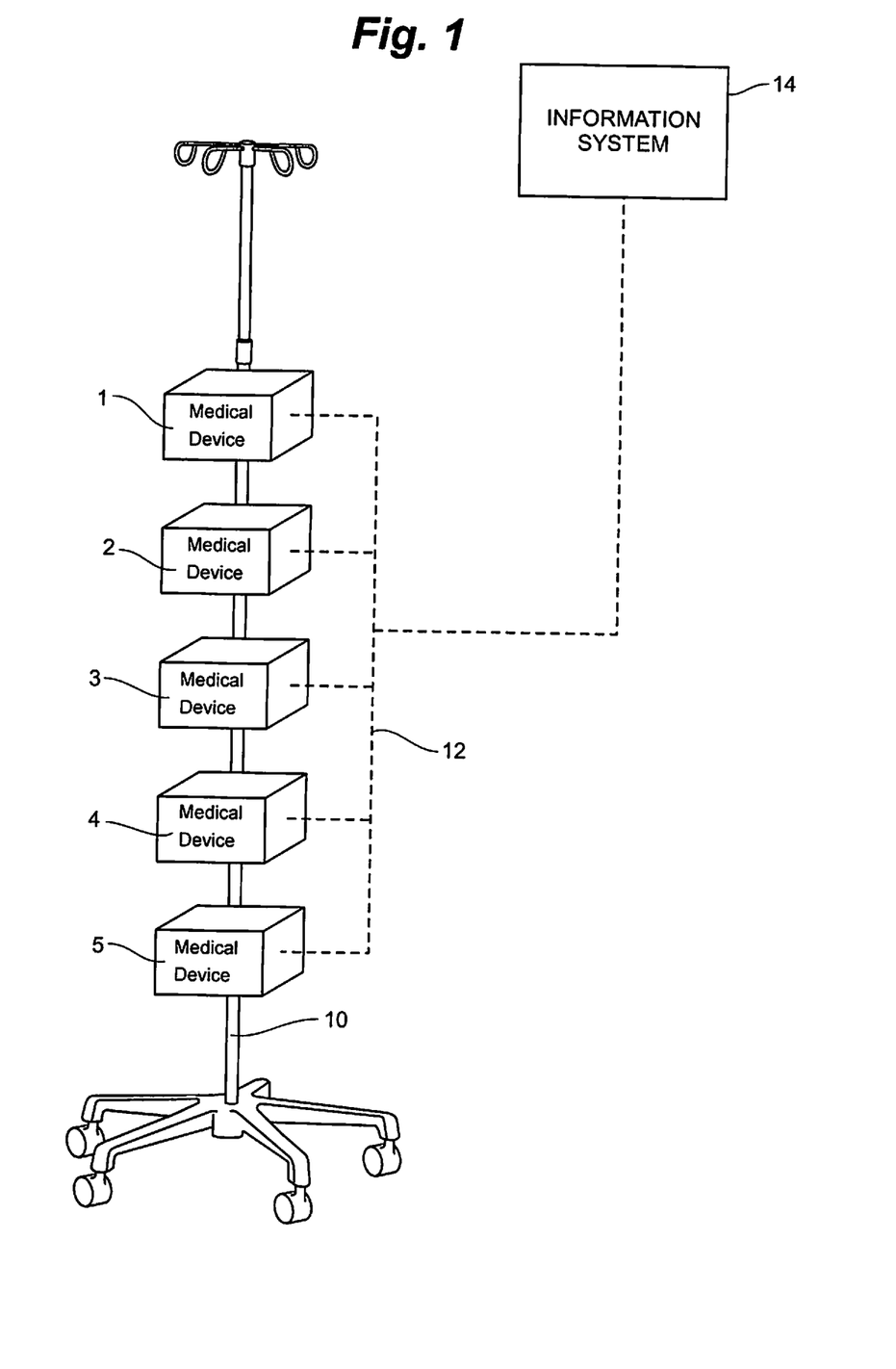
FIG. 1 is a schematic illustration of an example of several medical devices mounted to a common support structure.

FIG. 1 is a schematic illustration of an example of several medical devices 1-5 mounted to a common support structure 10 such as a pole or a rack. Individual medical devices 1-5 can be any appropriate medical devices that may be advantageously controlled in association with other medical devices. A quantity of five medical devices 1-5 is shown merely by way of example, and systems and methods of the present disclosure can include any appropriate number of medical devices. Medical devices 1-5 can be heterogeneous or homogeneous in type or model of device. In some examples, some or all of medical devices 1-5 are infusion pumps. Common support structure 10 can be an IV (intravenous) pole or infusion pump rack. Medical devices 1-5 can be communicatively connected, via any appropriate communication infrastructure(s) 12, to each other and/or a computing or other information system 14. Although depicted in FIG. 1 as being external to the medical devices, it is to be appreciated and understood that such computing or information system or systems could reside in any location, such as externally or remotely in a hospital's IT infrastructure, or physically adjacent to or near the medical devices, or even internally within the devices themselves.

Communication infrastructure 12 can be any appropriate system for providing inter-device communication, such as a wired or wireless network. Information system 14 can be any appropriate system such as a Hospital Information System (HIS), Electronic Medical Records (EMR) system, a personal computer or other computing device, and so on. Information system 14 can include a communication interface communicatively coupled to communication infrastructure 12 and medical devices 1-5.

In conventional, known methods and systems of associating medical devices 1-5, a user might interact individually with each device 1-5 through the user interface of the device, for example, by making multiple button presses on a keypad while receiving feedback from a display. In some known methods and systems, the user might press buttons to enter a settings menu, then press buttons to scroll to an association function, then enter a common identification number or code, with such a sequence being repeated laboriously for each device. In contrast, the present disclosure provides systems and methods that may ease considerably the burden on a user when associating devices.

Figure 2:
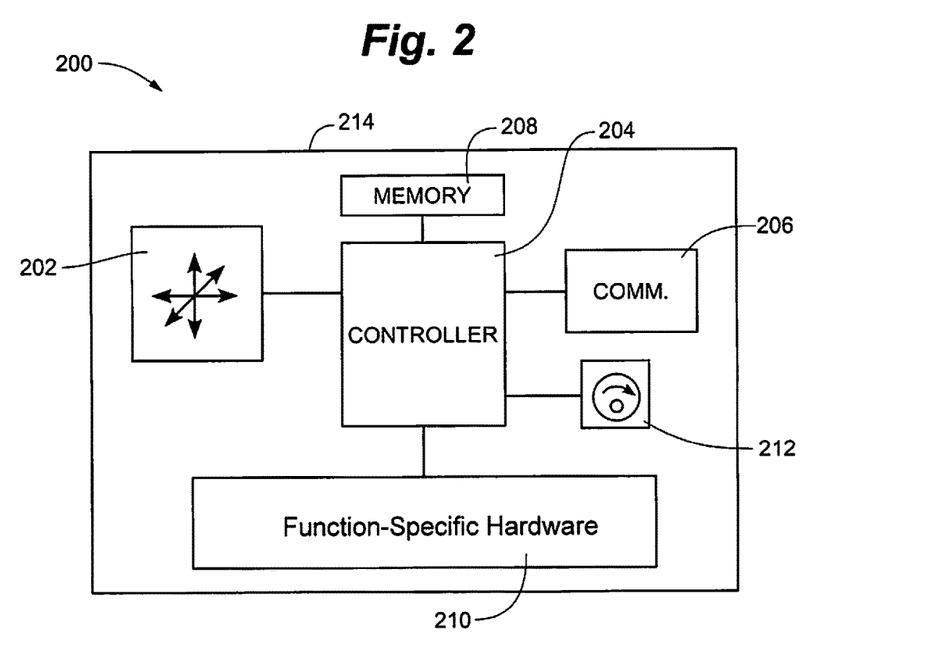
FIG. 2 is a schematic illustration of an example of a medical device that includes features to provide relatively quick and convenient association with other medical devices.

FIG. 2 is a schematic illustration of an example of a medical device 200 that includes features that can provide relatively quick and convenient association with other medical devices. Any or all of the examples of medical devices 1-5 of FIG. 1 can be provided as, or can include features of, medical device 200. Medical device 200 can include an accelerometer 202 configured to measure spatial accelerations of the device, a controller 204 operatively coupled to accelerometer 202, and a communication interface 206 operatively coupled to controller 204. Communication interface 206 can facilitate communication between medical device 200 and other medical devices, and/or communication with an information system as aforementioned via a communication interface of the information system, with examples of such communication links being illustrated in FIG. 1 generally as communication infrastructure 12. Communication interface 206 can include the use of any suitable communication technologies, architectures, protocols, and standards, etc., such as USB, TCP/IP, Ethernet, RS-232, WiFi, ZigBee, Bluetooth, NFC, IrDA, ANT, etc., and/or it can involve one or more novel and/or proprietary communication means.

Accelerometer 202 can include any suitable accelerometer components, and can include multiple components that provide information related to accelerations experienced by the medical device. Accelerometer 202 can measure and provide acceleration information in any appropriate numbers of degree of freedom in, for example, up to three translational axes and up to three rotational axes. In some examples, accelerometer 202 is configured to measure acceleration in a single axis. In some examples, accelerometer 202 is configured to measure acceleration in more than one axis. In some examples, accelerometer 202 is configured to measure acceleration in fewer than three axes. In some examples, accelerometer 202 is configured to measure and provide only translational acceleration information, and in some other examples, accelerometer 202 is configured to measure and provide only rotational acceleration information. In some examples, accelerometer 202 is configured to measure and provide translational acceleration information along orthogonal horizontal axes when the medical device 200 is in a standard, upright orientation. Accelerometer 202 can be based upon any suitable acceleration sensing technology or technologies.

In some examples, medical device 200 can include a magnetometer that can provide information relating to magnetic flux along one, two, or three axes, which can be orthogonal axes. A magnetometer can be used to measure changes in spatial orientation, providing a capability that can complement or supplant rotation information provided by a rotational accelerometer/gyroscope component. In some examples, accelerometer 202 can include a magnetometer.

Controller 204 can be any suitable controller, microcontroller, microprocessor, or the like. Controller 204 can include or be operatively coupled to a memory 208 of medical device 200. Memory 208 can be any suitable memory of any suitable capacity, and can be a non-volatile memory such as flash, EEPROM, and so on. Memory 208 can store any suitable information, such as information relating to acceleration patterns measured by accelerometer 202, executable code, operational parameters, and so on. Controller 204 of medical device 200 can be configured and programmed to execute, command, and/or perform any suitable actions, tasks, steps, and/or methods for controlling the medical device. Other controllers or processors (not shown) can also be employed in device 200 (for example, accelerometer 202 and/or communication interface 206 can include one or more dedicated processors). Regardless, these other controllers or processors can be considered part of the controller or microprocessor component 204 of FIG. 2.

Various features of medical device 200 are illustrated as being linked by lines, which schematically indicate operative couplings and/or communication links between said features. The operative couplings indicated by the lines should not be considered limiting, and any appropriate operative couplings between features/components can exist. For example, while FIG. 2 may topologically appear to illustrate memory 208 as being operatively coupled to accelerometer 202 through controller 204, this is merely for convenience of illustration, and memory 208 and accelerometer 202 can be coupled directly, or through a bus, etc.

Medical device 200 can include any appropriate function-specific hardware 210 to provide its intended functions as a medical device. In some examples, medical device 200 can be an infusion pump, and function-specific hardware 210 can include any or all of a pump mechanism, valves, sensors, application-specific integrated circuits (ASICs), firmware, and any other appropriate components. In some examples, medical device 200 can be a patient-monitoring apparatus such as a blood pressure monitor; and function specific hardware 210 can include a pressure cuff, hose, air pump, sensors, ASICs, firmware, and any other appropriate components.

Medical device 200 can include a housing 214. Any of the features of medical device 200 can reside within or otherwise be associated with housing 214, whether internally or externally thereto.

The present disclosure contemplates the use of information from accelerometers such as accelerometer 202 of device 200 in methods for associating medical devices. In an illustrative example 300 of FIG. 3, a plurality of medical devices can be provided at 302. The medical devices can be like, for example, devices 1-5 of FIG. 1, which can each be configured like, for example, device 200 of FIG. 2. Each of the medical devices could include an accelerometer 202 configured to measure spatial accelerations of the respective medical device. The discussion of method 300 herein includes citations to reference numerals of FIGS. 1 and 2, but this is merely by way of illustrative example and should not be construed as limiting method 300 to the specific arrangements of FIGS. 1 and 2. As may be appreciated by those of ordinary skill in the art, method 300 may be practiced on differing but compatible arrangements and instances of medical devices and systems.

Figure 3:
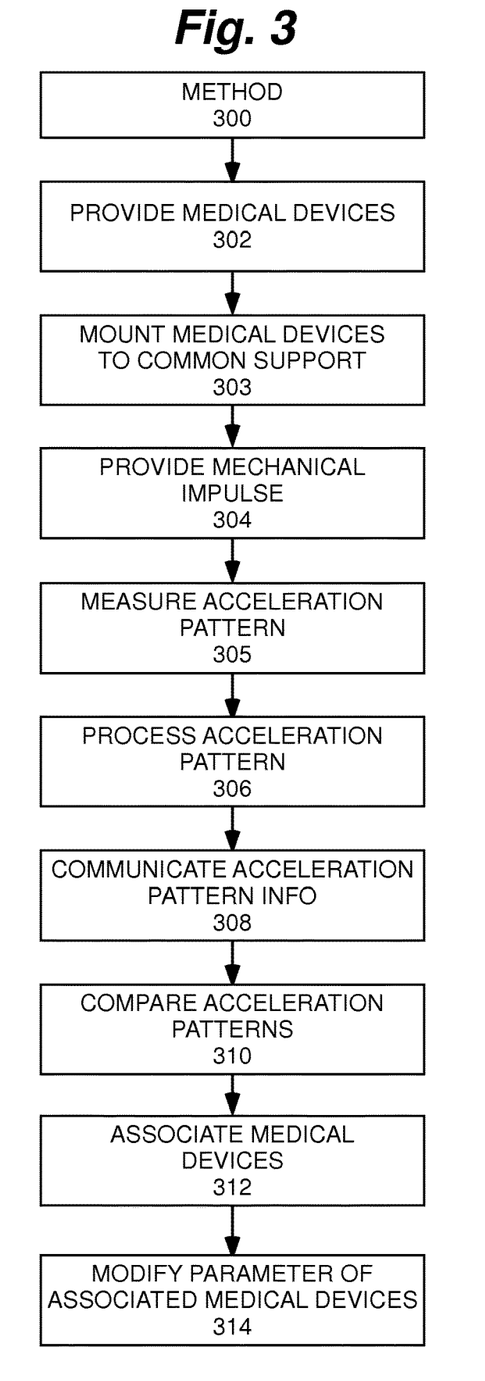
FIG. 3 is a schematic flow diagram of a method for associating medical devices.

The plurality of medical devices provided at 302 can include medical devices in an association-accepting mode. In some cases, the plurality of medical devices includes only devices that are in an association-accepting mode. A medical device can be configured to enter an association-accepting mode in any appropriate manner. In some examples, a medical device can be commanded to enter an association-accepting mode through input via a user interface. In some examples, a medical device can be configured to enter an association-accepting mode when powered-on from an unpowered or standby state. In some examples, a medical device can be commanded to enter an association-accepting mode after receiving a communication via a communication interface. In some examples, information system 14 manages which of medical devices 1-5 are in association-accepting mode.

In an association-accepting mode, a medical device is available to be associated with one or more other medical devices, if appropriate conditions are met to establish the association, as discussed further herein. In some examples, a medical device can be associated with more than one group or set of medical devices concurrently and a medical device in an association-accepting mode is available to be associated with a new group or set of medical devices in addition to any pre-existing associations that may be in effect at a given time. In some other examples, a medical device can only be associated with one group or set at a time. As a sub-example, a medical device that can only be associated with one group or set that is in an association-accepting mode can retain a pre-existing association until a new association is established, upon which any pre-existing association is relinquished. As another sub-example, a medical device that can only be associated with one group or set relinquishes any pre-existing association when it enters an association-accepting mode, regardless of whether a new association is established subsequent to having entered the association-accepting mode.

At 303, method 300 can include mounting medical devices 1-5 to a common support structure 10. The medical devices 1-5, common support structure 10, and the mechanism(s) and manner by which the medical devices are mounted to the support structure can be configured and structured such that mechanical impulses, motions, and vibrations are coupled and transmitted between the medical devices through the support structure. These components and aspects of the system of medical devices and common support structure can be designed with minimal mechanical damping therebetween that might reduce the sensitivity of the accelerometers 202 of the medical devices for measuring accelerations that may be experienced in common between the medical devices.

At 304, method 300 can include intentionally imparting a mechanical impulse, in any appropriate way, to the plurality of medical devices 1-5. The mechanical impulse can be transmitted between all of the plurality of medical devices 1-5 through the common support structure 10. In some instances, the mechanical impulse can be produced by manually striking the common support structure 10 or one or more of the medical devices 1-5, for example, with a slap or knock of a hand, or a kick of a foot. In some instances, a clinician may kick an IV pole to which multiple infusion pumps and/or other medical devices are mounted. As used in the present disclosure, a mechanical impulse can refer to an application of force over time (during which the force may vary) that can result in acceleration of objects to which the impulse is applied (directly or by way of mechanical coupling to another object).

Accelerations and associated motions resulting from mechanical impulses imparted to medical devices in methods and systems of the present disclosure may be substantially translational in various examples, but this is not necessary. Accelerations and associated motions may be substantially rotational in some cases, and in some examples, may include significant components of both translational and rotational motions. In some examples, a clinician can rotate (via an imparted torque) a common support structure 10 (such as a wheeled IV pole) to which medical devices 1-5 are substantially rigidly attached, such that all the medical devices experience substantially similar rotational accelerations and rotational displacements.

In some examples, one or more of the medical devices 1-5 can include a component 212 configured to produce a mechanical impulse, and the mechanical impulse imparted to the plurality of medical devices could be generated by component 212. Component 212 can be any suitable apparatus capable of generating a mechanical impulse of sufficient magnitude detectable by accelerometers 202 of medical devices mounted to the common support structure 10. Component 212 could be, for example, a motor-driven or other variety of vibrator, a loudspeaker driven at low frequency, or a solenoid selectively actuatable by controller 204, or it could be a manually-actuatable device.

In some examples, an incidental or unintentional mechanical impulse, or some other common motion experienced by the plurality of medical devices and measurable by the accelerometers of the medical devices, may be used in some of the contemplated methods for associating medical devices.

At 305, method 300 can include any of the medical devices measuring with their accelerometers 202 an acceleration pattern with respect to time, where the acceleration pattern can be due to the mechanical impulse of method element 304. As a matter of semantics, measuring an acceleration pattern may be said equivalently to be performed by a medical device 200 using its accelerometer 202, or performed by the accelerometer 202 of a medical device 200.

At 306, method 300 can include, for each medical device of the plurality of medical devices, the controller 204 of each medical device being configured and programmed to process the acceleration pattern measured (305) by the accelerometer 202 of the medical device relating to a mechanical impulse incident upon the device. Processing 306 can involve any suitable actions relating to the acceleration pattern. It can include recognition that an acceleration pattern of potential relevancy is occurring (or has occurred) and triggering of subsequent processing steps. Such recognition and triggering can be realized in any appropriate manner, for example, when a measured acceleration exceeds a pre-determined magnitude, or when a pre-determined pattern of acceleration vs. time is recognized. In some instances, the mechanical coupling between medical devices 1-5, the sensitivity of accelerometers 202, the recognition and triggering algorithms, and any other relevant factors can be configured such that if one of medical devices recognizes an acceleration pattern as being potentially relevant, the other devices likely will experience, and correspondingly recognize as potentially relevant, an acceleration pattern as well.

The processing 306 can include recording or storage of information relating to the acceleration pattern in memory 208 or any other suitable data storage means, but this may not be necessary. Processing 306 can include (re)packaging, defining, transforming, or otherwise generating information relating to an acceleration pattern from raw data provided by accelerometer 202. Raw data can be defined as all unaltered acceleration measurements sampled by accelerometer 202 over a time interval. Information relating to an acceleration pattern may be any suitable information. In some instances, information relating to an acceleration pattern may be raw data. In some cases, so-called "lossy" or "lossless" data compression may be applied to raw data. In some examples, processing can include subjecting raw data to Fourier decomposition, wavelet analysis, or any other suitable mathematical or signal processing technique or techniques that can produce, compute, or otherwise generate information relating to the acceleration pattern that describes the acceleration pattern and that can be more concise than raw data and/or potentially more easily used to compare the acceleration pattern with other observed acceleration patterns. In the present disclosure, information relating to an acceleration pattern may be referred-to in shorthand as "the acceleration pattern".

At 308, method 300 can include each or some of the plurality of medical devices communicating, via communication interface 206, information related to the acceleration pattern measured by its accelerometer 202 and processed by its controller 204. The information can be communicated to any other suitable entities, such as others of the plurality of medical devices, and/or to an information system 14, any of which can be configured and programmed to receive information related to acceleration patterns.

At 310, method 300 can include comparing for correspondence, according to defined correspondence criteria, relevant acceleration patterns measured by the at least two of medical devices. Comparing 310 can be performed by any suitable device or system. In some examples, comparing 310 can be performed by information system 14. In other cases, comparing 310 could be performed by one of the medical devices that acts, at least with regard to comparing 310, as a master device. One of the devices can be designated in advance as a master device, or such a designation can be performed in an ad-hoc manner. Performance of comparing 310 can include the transmission or communication of information related to acceleration patterns to a device or system, such as information system 14. Such transmission or communication can take place at 308 or 310 without loss of generality.

Any suitable techniques and/or algorithms can be employed for comparing the relevant acceleration patterns for correspondence. Comparing 310 can include any appropriate manipulations of information relating to acceleration patterns, such as scaling acceleration patterns—for example, because different medical devices may experience the same impulse event, but with different local magnitudes at the devices—or performing coordinate transformations on acceleration patterns—for example, because different medical devices may be mounted to a common support structure (e.g., an IV pole) in different orientations (e.g., facing different directions) such that the local coordinate system of their accelerometers may differ. Manipulations such as scaling or transforming coordinates of a measured acceleration pattern can be performed by an information system, and/or by a medical device that measured the acceleration pattern being scaled or transformed. When performed by a medical device, scaling or transforming also can be considered to be a part of processing (306) the acceleration pattern.

Any appropriate defined correspondence criteria can be used. Comparing for correspondence could, for example, include calculating a similarity/difference score for acceleration patterns measured by different medical devices, and a defined correspondence criterion could be the similarity/difference score falling in a defined range.

An outcome of comparing (310) the acceleration patterns measured by accelerometers 202 of the medical devices can be the defining, enumerating, listing, or otherwise arriving at a set or group of medical devices that are determined to have measured acceleration patterns that correspond according to defined correspondence criteria. At 312, method 300 can include associating all of the medical devices that measured acceleration patterns that satisfy the defined correspondence criteria. When the comparing (310) is performed by an information system 14, associating (314) can include the information system communicating an associating message to at least each of the plurality of medical devices that measured acceleration patterns that satisfy the defined correspondence criteria. Similarly, in cases when comparing (310) is performed by one of the medical devices, such communication can be performed by that medical device. The associating message can include any appropriate information. It may include, for example, any of a list of the medical devices that are members of the associated set or group, information related to one or more measured acceleration profiles, and so on. The associating message can include information relating to a hospital or clinic, such as a location in the facility, and can include information relating to a patient in whose care the medical devices may be deployed, such as a patient identification or medical record number. Associating (312) can also include the medical devices that are being associated receiving the associating message via communication interfaces 206. The controllers 204 of the medical devices can be configured and programmed to receive such associating messages, and take any appropriate action to make the operation of the medical device consistent with being associated with the other members of the associated set of medical devices, including, for example, modifying a parameter of the medical device to denote the device as being a member of the associated group.

Although associating (312) can include, as described herein, communicating an associating message to each medical device that is a member of the set of associated devices, and/or the controller 204 of each member medical device modifying a parameter of the medical device to denote the device as being a member of the associated group, these are not necessary in all examples for the system and method of the present disclosure. In some examples, individual medical devices may be "unaware" that they are members of an associated group; for example a particular device may not locally have any setting or parameter that indicates that it is a member of an associated group. In some examples, a listing of members of a group or set of associated medical devices can be maintained at or in an information or computing system and not at the medical devices, or in the case where one of the medical devices acts as a master device, at the master device and not at the other medical devices.

At 314, method 300 can include modifying a parameter of each member of a set or group of devices that are associated. Any appropriate parameter can be modified, and can be an operational parameter that affects the operation of the medical device, in accordance with how the device is configured and programmed to respond to possible values of the parameter. In various examples, the modification of the parameter can be achieved in different ways.

In examples where each individual devices possesses the information that it is member of a particular group ("Group I" in this example), a message could be broadcast from any appropriate source (which can be information system 14 or one of the medical devices belonging to the group, for example) to at least all members of Group I, and possibly to other devices as well, identifying it as a message for members of Group I. The individual devices that are members of Group I could then identify the message as intended for them, and modify the parameter in question. In cases where an associating message is sent, an instruction to modify a parameter can be included with the associating message.

In other examples, individual medical devices may not possess the knowledge of the group(s) of which they are members. In such an example, an information or computing system or a master device could send messages specifically addressed to individual members of the group, instructing them to modify the parameter in question.

Other ways of performing aspects of method 300 are contemplated. In some examples, aspects of comparing (310) acceleration patterns and associating (312) medical devices can be performed in a distributed manner among medical devices. In one example, a first medical device can communicate (308) information related to an acceleration pattern measured with its accelerometer to the other medical devices. A second medical device can receive the information transmitted by the first medical device and compare (310) it with information related to an acceleration pattern measured with its own accelerometer. If defined correspondence criteria are met, the second medical device can associate (312) itself with the first medical device. The second medical device can communicate a message announcing its association with the first medical device, and the second medical device can communicate (308) information related to the acceleration pattern measured with its accelerometer to the other medical devices. Each other medical device can similarly compare (310) received acceleration pattern information with its own acceleration pattern information for satisfaction of defined correspondence criteria, and associate (312) with other medical devices if appropriate. This is just one example of how aspects of associating medical devices could be performed in a distributed manner.

The present disclosure contemplates, in some examples, the use of acceleration pattern information measured after members of a group or set of medical devices are already associated. Later corresponding acceleration patterns measured by medical devices (after an earlier association of medical devices) could be used to verify that members of an associated set of medical devices continue to be coupled to a common support structure. For example, if seven medical devices are associated at an earlier time, and subsequently only six of the medical devices communicate information relating to later corresponding acceleration patterns, the one medical device of the group of seven that did not communicate such information could be (at least provisionally) presumed to be missing from the group, and appropriate actions(s) can be made to address the situation. In some examples, a verification function could be actively engaged (for example, a clinician selects a verification mode, then imparts an impulse to a group of medical devices). In some examples, a verification function could run as a background function and could verify group associations with acceleration patterns that may result from incidental or unintentional mechanical impulses. For example, multiple associated medical devices could be mounted to a common IV pole. The IV pole might subsequently be moved to a different position, and the acceleration patterns experienced during the motion could be compared for verification.

In some instances, acceleration information could be used to infer information about relative positions of medical devices mounted to a common support structure. In one example, a plurality of medical devices can be mounted to a common support structure at different heights, as illustrated for devices 1-5 on common support structure 10. Common support structure 10, with mounted devices 1-5, could be tilted (rotated) away from vertical about a rotation axis close to the ground (although in other examples, other rotation axes could be used). In such a motion, a device further from the rotation axis such as device 1 would experience more motion and greater accelerations than a device closer to the rotation axis such as device 5. The differing acceleration profiles due to the differences in distance from the rotation axis could be used to determine the relative heights of the devices on the common support structure. Such a determination could be performed, for example, by the same information system 14 that compares acceleration profile information to associate medical devices. Such a determination could be performed as part of the association comparison/analysis, or it could be performed as a separate analysis. Subsequently, with relative heights of medical devices 1-5 known, the devices could be controlled or coordinated in a manner that takes the known relative heights into account. For example, user interfaces on the devices 1-5 could be commanded to produce a coordinated display in sequence from top to bottom, which could be more eye-catching for a user observing the coordinated display.

The disclosure should not be considered limited to the particular examples described herein, but rather should be understood to cover all aspects of the disclosure and equivalents thereof. Various modifications, equivalent processes, as well as numerous structures to which the disclosure can be applicable will be readily apparent to those of skill in the art upon review of the instant specification.

The invention claimed is:

1. A method for associating medical devices, the method comprising:
   mounting a plurality of medical devices to a common support structure;
   providing the plurality of medical devices, each of the plurality of medical devices including an accelerometer configured to measure spatial accelerations of the medical device;
   imparting a mechanical impulse to the plurality of medical devices, the mechanical impulse being transmitted between all of the plurality of medical devices through the common support structure to provide an acceleration pattern, wherein the imparting the mechanical impulse includes a component of one of the plurality of medical devices producing the mechanical impulse;
   measuring with the accelerometer included in each of at least two of the plurality of medical devices the acceleration pattern with respect to time;
   comparing for correspondence, according to a defined correspondence criteria, the acceleration patterns measured by the at least two of the plurality of medical devices;
   associating all of the at least two of the plurality of medical devices that measured the acceleration patterns that satisfy the defined correspondence criteria.

2. The method of claim 1, further comprising modifying a parameter of each medical device of the plurality of medical devices as being a member of an associated group.

3. The method of claim 1, wherein comparing includes scaling at least one of the acceleration patterns measured by the at least two of the plurality of medical devices.

4. The method of claim 1, wherein comparing includes performing a coordinate transformation on at least one of the acceleration patterns measured by the at least two of the plurality of medical devices.

5. The method of claim 1, wherein at least one of the plurality of medical devices includes an accelerometer that measures acceleration in more than one axis.

6. The method of claim 1, wherein at least one of the plurality of medical devices includes an accelerometer that measures acceleration in fewer than three axes.

7. The method of claim 1, wherein the plurality of medical devices includes medical devices in an association-accepting mode.

8. The method of claim 1, wherein comparing includes:
   each of the at least two of the plurality of medical devices transmitting the acceleration patterns measured by the at least two of the plurality of medical devices to an information system; and
   the information system comparing for correspondence, according to the defined correspondence criteria, the acceleration patterns transmitted from each of the at least two of the plurality of medical devices.

9. The method of claim 8, wherein associating includes:
   the information system communicating an associating message to at least each of the at least two of the plurality of medical devices that measured acceleration patterns that satisfy the defined correspondence criteria.

10. The method of claim 1, wherein comparing is performed in a distributed manner among the at least two of the plurality of medical devices.

11. The method of claim 1, wherein comparing is performed by one of the at least two of the plurality of medical devices.

12. The method of claim 1, wherein comparing includes at least a first one of the at least two of the plurality of medical devices transmitting information related to the acceleration pattern measured with the accelerometer included in the first one of the at least two of the plurality of medical devices.

13. The method of claim 12, wherein comparing includes at least a second one of the at least two of the plurality of medical devices comparing information related to the acceleration pattern measured with the accelerometer included in the second one of the at least two of the plurality of medical devices with information received from the first one of the at least two of the plurality of medical devices.

14. A system of medical devices, comprising:
a plurality of medical devices, each of the plurality of medical devices including:
an accelerometer configured to measure spatial accelerations of the medical device;
a controller operatively coupled to the accelerometer; and
a communication interface operatively coupled to the controller; and
an information system communicatively coupled to the communication interface of each of the plurality of medical devices,
wherein:
the controller of each of the plurality of medical devices is configured and programmed to:
process an acceleration pattern measured by the accelerometer of the medical device; and
communicate information related to the acceleration pattern to the information system via the communication interface;
the information system is configured and programmed to:
receive the information related to the acceleration patterns communicated by members of the plurality of medical devices;
compare for correspondence, according to a defined correspondence criteria, the information related to the acceleration patterns received by the information system;
maintain a list of at least each of the plurality of medical devices that communicated information related to the acceleration patterns that satisfies the defined correspondence criteria;
wherein at least one of the plurality of medical devices includes a selectively actuatable component capable of producing measurable accelerations in others of the plurality of medical devices when the plurality of medical devices are mounted to a common support structure.

15. The system of claim 14, wherein:
the information system is configured and programmed to communicate an associating message to at least each of the plurality of medical devices that communicated information related to the acceleration patterns that satisfies the defined correspondence criteria; and
the controller of each of the plurality of medical devices is configured and programmed to receive the associating message from the information system.

* * * * *